United States Patent [19]

Greenberg

[11] 4,437,461
[45] Mar. 20, 1984

[54] VALVE RESPIRATOR DEVICE

[76] Inventor: Mitchell H. Greenberg, 796 Sport Hill Rd., Easton, Conn. 06612

[21] Appl. No.: 368,934

[22] Filed: Apr. 16, 1982

[51] Int. Cl.³ ............................................. A61M 16/00
[52] U.S. Cl. ............................ 128/205.24; 128/204.21; 91/33; 415/125; 417/176; 137/865; 137/625.22; 137/625.65
[58] Field of Search .................... 128/28, 30, 30.2, 38, 128/40, 203.27, 204.17, 204.18, 204.21, 205.24, 205.18, 205.19, 205.23; 91/33; 415/125; 417/176; 137/865, 870, 625.2, 625.21, 625.22, 625.65

[56] References Cited

U.S. PATENT DOCUMENTS

| | | | |
|---|---|---|---|
| 2,223,590 | 12/1940 | Alden | 137/625.22 |
| 2,398,542 | 4/1946 | Light | 137/625.21 |
| 3,007,494 | 11/1961 | Henzl | 137/625.65 |
| 3,120,228 | 2/1964 | Huxley | 128/30.2 |
| 3,149,641 | 9/1964 | Norton | 137/625.65 |
| 3,638,926 | 2/1972 | Melville et al. | 128/203.27 |
| 4,076,021 | 2/1978 | Thompson | 128/205.18 |
| 4,239,039 | 12/1980 | Thompson | 128/205.24 |

OTHER PUBLICATIONS

Bruno, Alien Property Custodian-S.N. 347,414, 5/11/43.

Primary Examiner—Henry J. Recla

Attorney, Agent, or Firm—Caesar, Rivise, Bernstein & Cohen, Ltd.

[57] ABSTRACT

A valve respirator device for use both on human and on animal patients. The device comprises a housing having an inport, an outport and an exhaust port. The outport is connected to the patient's respiratory system, the inport is connected to a source of air and the exhaust port is open to the surrounding atmosphere. To that end, in alternating succession, first the inport and then the exhaust port is in fluid communication with the outport. A slotted, rotatable valve cylinder is utilized as a means for providing alternating fluid communication first between the inport and the outport and then between the outport and the exhaust port. The device further comprises a metering plate which is interposed in the path of fluid communication between the outport and the other two respective ports. In that regard, the metering plate includes several apertures which regulate the volume and other flow characteristics of air passing between these respective ports. The device is constructed as a modular assembly so that the various component parts comprising the device may readily be substituted for, cleaned or repaired. Flow characteristics of the device may readily be changed by using interchangeable metering plates or valve cylinders. Other features of the device include heating means, warning means which signal a malfunction in the device, a pressure relief valve for preventing overinflation of the patient's lungs and an exhaust port valve for regulating the patient's exhalation rate.

24 Claims, 13 Drawing Figures

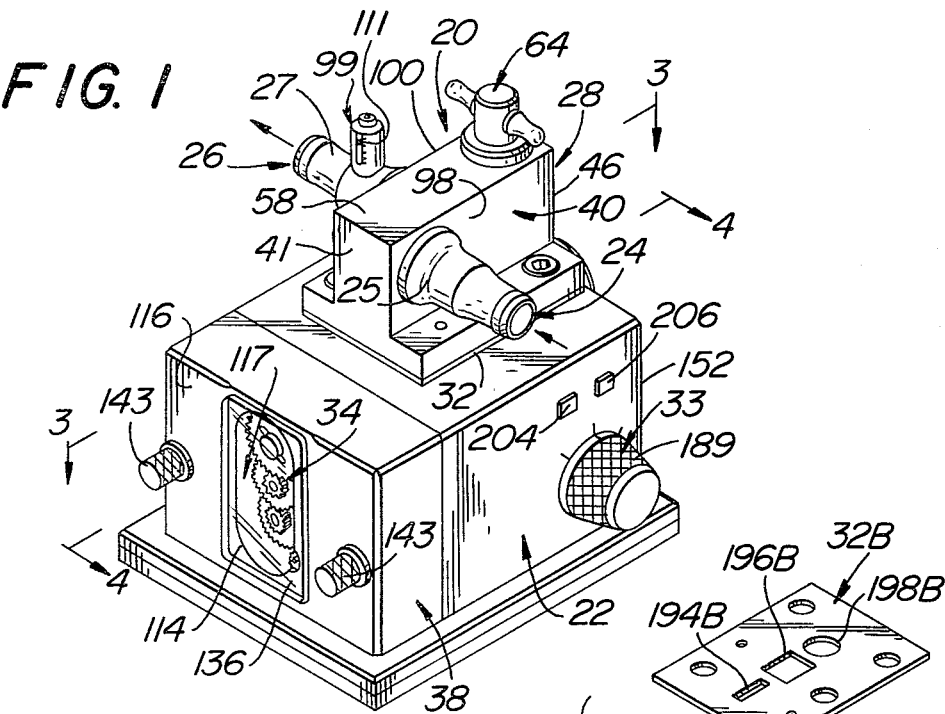
FIG. 1
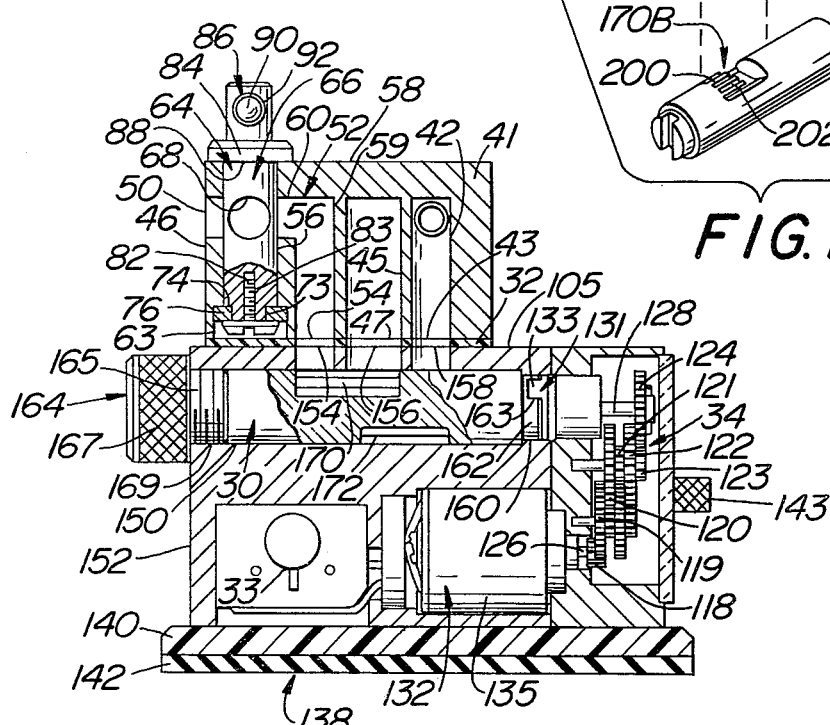
FIG. 12
FIG. 4

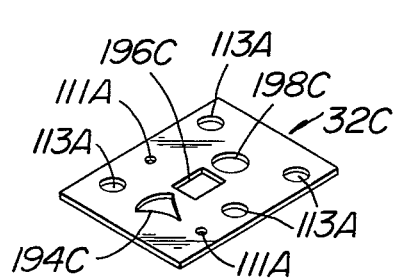
FIG. 13
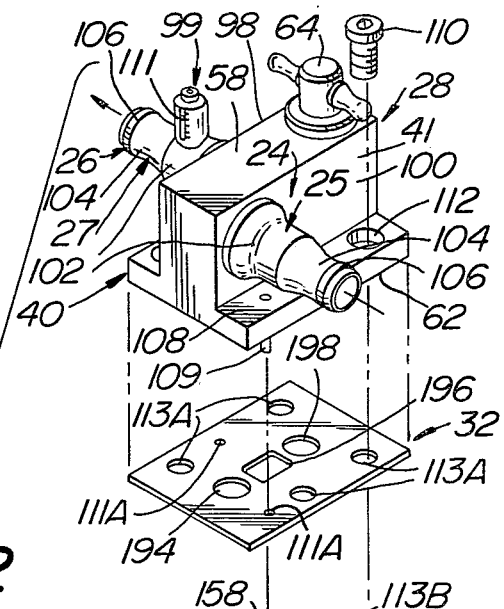
FIG. 2
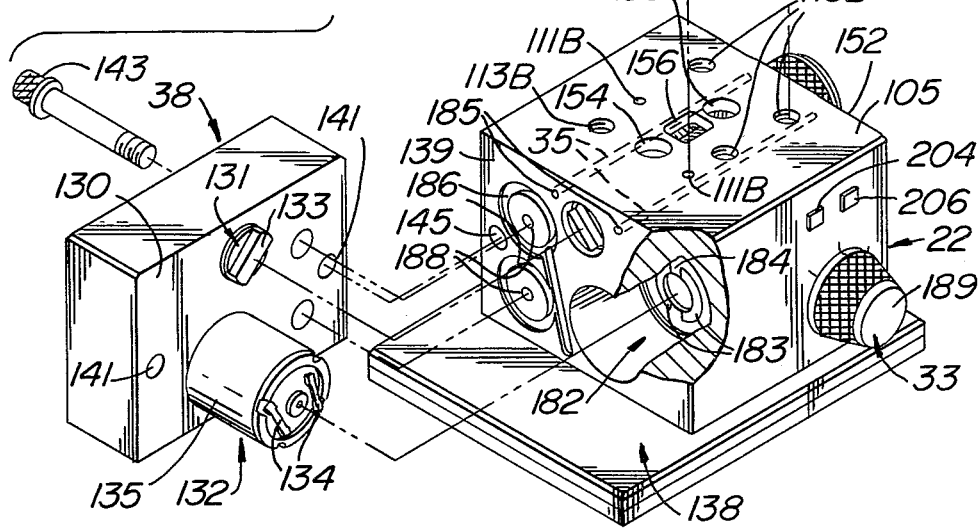
FIG. 9
FIG. 11

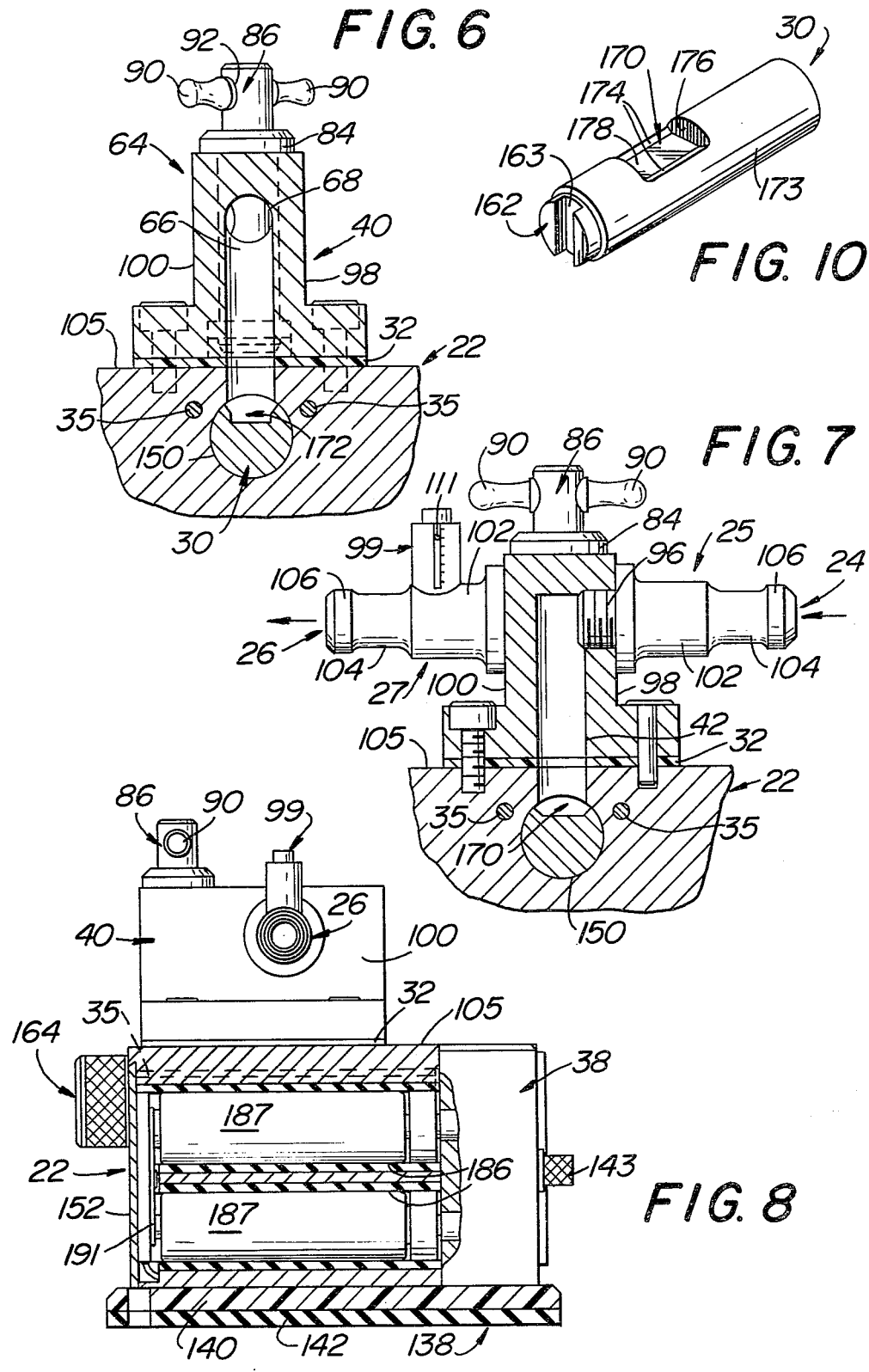

VALVE RESPIRATOR DEVICE

BACKROUND OF THE INVENTION

This invention relates generally to medical devices, and more particularly to a respirator device which can be used on people as well as on animals.

There is a substantial need for respirator devices which are compact, portable and inexpensive to produce. Such devices provide means for administering emergency respiratory aid to a patient either at an accident scene, at a first aid station or at a medical office whose size or location is such that the use of a larger, more expensive respirator unit would either be unfeasible, impractical or too expensive.

The instant invention provides a means for automatically controlling the air flow into and out of a patient's lungs in order that the patient's lungs may be aerated smoothly and in as close to a normal physiological pattern of respiration, as can reasonably be attained. To that end, normal respiration requires that at regular predetermined intervals the patient be alternately provided with air for inhalation, followed by an interval during which time the patient is able to exhale air from his or her lungs.

Respirator devices are used in a variety of different situations. For instance, these devices may be used to assist a patient suffering from either a chronic or an acute illness or one who has sustained a traumatic injury (e.g., smoke inhalation), in performing his or her respiratory functions. This is achieved by providing pressurized, (often filtered and sometimes oxygen enriched) air to the patient in a normal physiolgical pattern of respiration (i.e., a pattern whereby a predetermined inhalation interval is followed by a predetermined exhalation interval).

Respirator devices are also frequently used for assisting a patient's respiratory functions during surgery or while the patient is undergoing various other medical procedures. With regard to surgery, the respirator device provides a means for administering an anesthetic gas and air mixture for the patient to breath during the procedure.

Notwithstanding the fact that in an operational setting (as mentioned above), the gases passing through the device might include an anesthetic gas or have a higher concentration of oxygen than is normally found in atmospheric air, for purposes of the foregoing discussion the gases passing through the device will generally be referred to as "gas".

Although there are a number of compact artificial respirator devices disclosed in the prior art, none of these devices appear to be fully satisfactory. One such artificial respirator device is disclosed in U.S. Pat. No. 4,171,697 (Arion). However, the Arion device has several significant limitations or drawbacks. The device disclosed in the Arion patent is not completely portable in that it comprises a plurality of separate units, namely, a separate control unit and a separate power unit. Furthermore, the Arion device utilizes an elongated cylinder having a hollow core which would have a tendency toward clogging while the device is in operation. Moreover, the Arion device provides inadequate preventative means for insuring that the patient's lung do not accidentally collapse or become overinflated while the device is being used.

Although there are a number of other artificial respirator devices disclosed in the prior art, these devices generally tend to be rather complex, not very portable (in spite of the fact that some of these devices are characterized by their respective inventors as being portable) and not well adapted for enabling one to expeditiously change the volume or other flow characteristics of the air passing through the device. Moreover, these devices generally utilize parts which are not readily removable for purposes of cleaning, servicing or replacement.

For example, in U.S. Pat. No. 4,210,136 (Apple) there is disclosed a piston operated ventilation unit which utilizes a mechanically complex variable radius crank arm as a means for changing the volume capacity of the pump. Although this device to a limited degree may be suitable for its intended purpose, it is quite complex thereby increasing manufacturing costs and rendering it more likely to mechanical failure than a less complex system.

Various other respirator devices are disclosed in U.S. Pat. Nos. 2,930,375 (Early); 4,203,434 (Brooks); 3,265,061 (Gage, Jr.) and 4,076,021 (Thompson).

OBJECTS OF THE INVENTION

Accordingly, it is a general object of the invention to provide a device which overcomes the disadvantages inherent in prior art respirator devices.

It is a further object of the invention to provide a respirator device which is constructed as a modular assembly, thus enabling one to readily either replace, service or clean the component parts comprising the device.

It is still a further object of the invention to provide a respirator device which is both portable in nature and capable of being used on both human as well as on animal patients.

It is still a further object of the invention to provide a valve respirator device which utilizes interchangable means for readily varying the volume and other flow characteristics of the fluids passing through the device.

SUMMARY OF THE INVENTION

These and other objects of the instant invention are acheived by providing a compact respirator device. The device comprises a housing having a first, a second and a third port, with the first port in fluid communication with a source of gas, the second port open to the surrounding atmosphere and the third port in fluid communication with a patient's respiratory system. The device includes moveable means for alternately establishing fluid communication first, between the first port and the third port and then between the second port and the third port. To that end, when the first port is in fluid communication with the third port the patient inhales the gas passing through the first port and when the second port is in fluid communication with the third port the patient is able to exhale gas therethrough to the ambient atmosphere. The device further includes means for regulating the amount of gas passing through each of the respective ports as well as means for regulating the time intervals during which the first port and the second port, respectively, are in fluid communication with the third port.

DESCRIPTION OF THE DRAWING

FIG. 1 is a perspective view of a compact respirator device constructed in accordance with this invention;

FIG. 2 is an exploded perspective view, partially in section, of the device shown in FIG. 1;

FIG. 4 is an enlarged sectional view of the device taken along line 4—4 of FIG. 1;

FIG. 6 is an enlarged sectional view of the device of the invention taken along line 6—6 of FIG. 4;

FIG. 7 is an enlarged sectional view of the device taken along line 7—7 of FIG. 5;

FIG. 8 is a sectional view of the device taken along line 8—8 of FIG. 3;

FIG. 9 is an enlarged perspective view of the slotted valve cylinder showing an exhaust port slot;

FIG. 10 is an enlarged perspective view of the slotted valve cylinder of the invention showing its outlet port slot;

FIG. 11 is an enlarged perspective view of a slotted valve cylinder having a ribbed inlet port slot;

FIG. 12 is a perspective view of a valve cylinder with a ribbed inlet port slot and its complementary metering plate; and FIG. 13 is a perspective view of an alternatively constructed metering plate.

DETAILED DESCRIPTION OF THE PREFERRED EMBODIMENT

Figure 3:
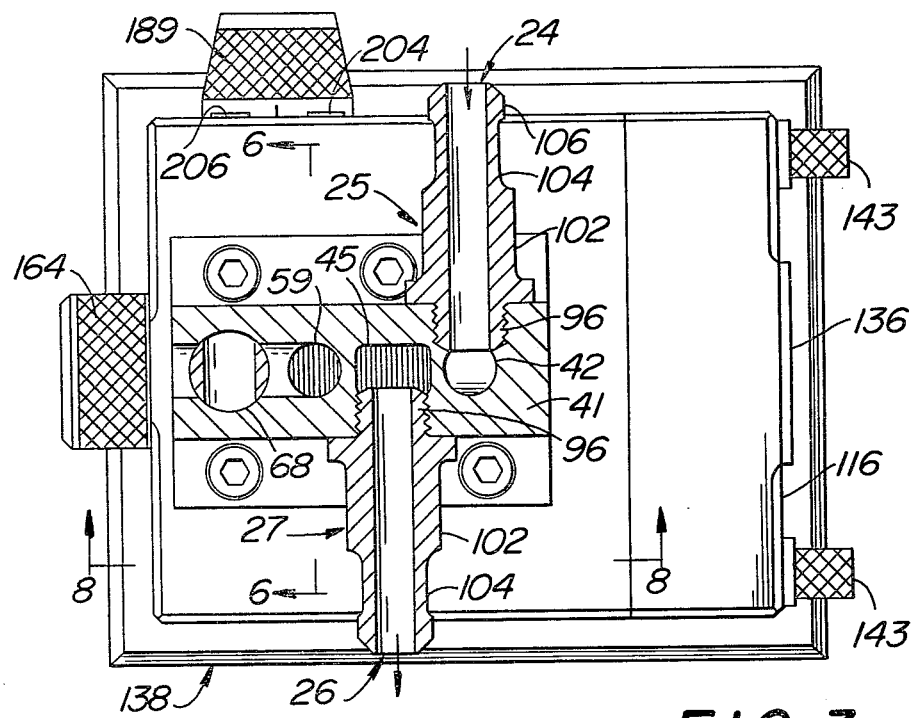
FIG. 3 is an enlarged sectional view of the device taken along line 3—3 of FIG. 1.

Referring now to the various figures of the drawing wherein like reference characters refer to like parts, there is shown at 20 a compact respirator device constructed in accordance with the instant invention. The device 20 is designed to assist a patient's respiratory process by providing the patient (either human or animal) with air for breathing. The device operates in a conventional inspiratory-expiratory cycle. To that end, the patient is in alternating succession, first provided with air to be inhaled (the inspiratory phase) followed by an interval during which time the patient is able to exhale the air through the device (the expiratory phase). Moreover, the device can be used for providing the patient with an anesthetic gas in combination with the air and can be used to regulate the amount as well as the other flow characteristics (e.g., pressure) of gas (air or air-anesthesia gas mixture) which is inhaled and then later exhaled by the patient.

To that end, the device 20 is used in combination with a source of gas, which through a first tube is connected to what shall be referred to as the inlet port of the device. A second tube is used to connect, typically a breathing mask (which fits over the patient's nose and mouth), to what shall be referred to as an outlet port of the device.

As shown in FIGS. 1 and 2, the valve respirator device 20 basically comprises a body 22, an inlet port 24, an outlet port 26, an exhaust port 28, a slotted valve cylinder 30 (shown in FIG. 10), metering means 32, control means 33 and rotational means 34.

The respirator device 20 is arranged to control the air flow both into and out of a patient's lungs in order that the patient's lungs may be aerated smoothly and efficiently. In that regard, during the inspiratory phase of the breathing cycle, the outlet port is brought in fluid communication with the inlet port 24 by the valve cylinder. During the expiratory phase, the outlet port is brought into communication with the exhaust port 28. In particular, the device 20 intermitently causes pressurized gas to flow from the inlet port 24 to the outlet port 26 during a first portion of a rotational cycle of the valve cylinder (to be explained later) and then from the outlet port to the exhaust port 28 during a second portion of this cycle. During the phase that the inlet port 24 is in fluid communication with the outlet port 26, the patient inhales the gas being supplied to the inlet port while and during the phase that the outlet port 26 is in fluid communication with the exhaust port 28, the patient exhales air from his lungs to the surrounding atmosphere. A pair of slots or recesses in the periphery of the valve cylinder 30 provide the means for alternately establishing fluid communication between the outlet port 26 and the inlet port 24 and then establishing fluid communication between the outlet port 26 and the exaust port 28 as the valve cylinder 30 is rotated by the rotational means 34.

The metering plate 32 is interposed in the path of fluid flow between the outlet port 26 and the inlet port and exhaust ports 24 and 28, respectively, to provide a means for regulating or changing the flow characteristics of the gas passing from either the inlet port 24 to the outlet port 26 or from the outlet port to the exhaust port 28.

The device 20 is compact in the interest of portability and is also of a modular construction for ease of assembly/disassembly, cleaning, repair, etc. Insofar as size is concerned, the device is extremely compact and can be held within one's hand. Regarding modularity (and as can be appreciated from FIG. 2), the device basically comprises four modular assemblies, namely, a valve assembly, a motor-gear assembly 38, a port assembly 40, and the metering plate 32. Each of these assemblies readily engages the other assemblies to form a single operational unit. The assemblies can be readily disconnected from one another to provide easy access means to the components in order that the components may readily be replaced, serviced, or cleaned.

In operation, an air supply (either portable or fixed), or alternatively, a blower unit (also either portable or fixed) supplies air, oxygen or other gas(es) under pressure to the inlet port 24.

Figure 5:
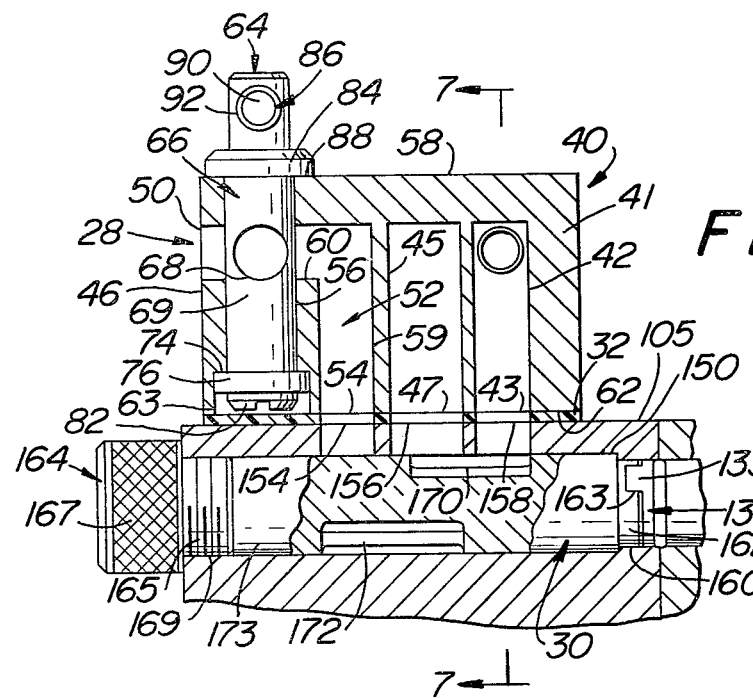
FIG. 5 is an enlarged side elevational view, partially in section, of an upper portion of the device.

As can be seen in FIGS. 2 and 5, the port assembly 40 comprises a block or body 41 having three ports and three passageways, with each of said passageways providing fluid communication between a respective port and a particular slot in the slotted valve cylinder 30 (which shall be discussed in detail later). In this regard, the inlet port 24 comprises a coupling 25 which is arranged to be disposed within the open end of a conduit or tube (not shown) from the gas supply (not shown). The coupling is in fluid communication with a cylindrically shaped passage 42 in the body 41. The passage 42 is also in fluid communication with a passage opening 43 on the bottom surface 62 of the port assembly block 41. As best shown in FIGS. 5 and 7, the passage 42 is disposed vertically in the block and is aligned to intersect and be in fluid communication with the horizontally disposed coupling 25.

The outlet port 26 comprises a coupling 27 which is similar in construction to coupling 25 and is in fluid communication with a generally rectangular, vertically disposed, passage 45 through the port assembly block 41. The passage 45 is located at a generally central position in the port assembly 40 and is aligned to intersect and be in fluid communication with the horizontally disposed coupling 27. The passage 45 also extends downward to an opening 47 on the bottom surface 62 of the port assembly block 41.

The exhaust port 28 comprises a valve regulated outlet opening 50 and is connected in fluid communication with an exhaust port passage 52. The exhaust port passage 52 is a generally cylindrical, inverted L-shaped passage in the port assembly block 41.

As best shown in FIG. 5, the exhaust port passage 52 comprises a vertical leg 59 and a horizontal leg 60. To that end, the vertical leg 59 extends upward from an exhaust port passage opening 54 on the bottom surface 62 of the port assembly block 41 to a point near the top surface 58 of the port assembly, where it merges with the horizontal leg 60. The horizontal leg portion of passage 52 terminates at an outlet opening 50 in the rear surface 46 of the port assembly block. The outlet opening 50 serves as the vent for exhaled gas to pass to the ambient atmosphere.

The flow of gas through the exhaust port 28 is controlled by an exhaust port valve 64. In that regard, the exhaust port valve controls the patient's rate of exhalation, and when properly set, prevents the patient's lungs from collapsing. The valve 64 is located in a vertical bore 56 which extends from the top surface 58 of the port assembly block adjacent its rear end. The bore 56 extends through the horizontal leg 60 of the exhaust port passage to the bottom surface 62 of the port assembly block. As can be seen in FIG. 5, the bore 56 enlarges so as to define an enlarged cylindrical cavity 63 adjacent the bottom of the block 41.

An exhaust port valve cylinder 66 is located in the exhaust port bore 56. As shall be described in greater detail below, the cylinder 66 serves as the means for controlling the passage of air from the exhaust port passage 52 to the exhaust port outlet opening 50. To that end, as shown in FIGS. 3, 4, 5, and 6, the exhaust port valve cylinder 66 includes a horizontally disposed valve opening 68, extending diametrically through the cylinder. The valve opening 68 is in vertical alignment with the horizontal passage portion 60 of the exhaust port passage. Moreover, the cross sectional area of the opening 68 is approximately equal to the cross sectional area of the horizontal leg 60 of the exhaust port passage.

The bottom portion 73 (shown in FIG. 4) of the cylinder 66 is of a reduced diameter from the remainder of the cylinder. In that regard, the interface between the narrow diameter bottom portion of the cylinder and the larger diameter remaining portion establishes a generally flat annular horizontal ledge 74.

A washer 76 whose diameter is larger than the diameter of the bore 56 is fitted about the narrower diameter bottom portion 73 of the cylinder. To that end, the washer 76 is positioned within the enlarged cavity 63, adjacent the bottom surface 62 of the port assembly. An externally threaded bolt 82 is threaded into an internally threaded screw hole 83 through the bottom surface of the cylinder 66 to secure the washer 76 to the cylinder 66 and against the annular horizontal ledge thus preventing the cylinder 66 from sliding upwardly through the bore 56. Moreover, the top surface of the washer 76 and the annular surface 74 are both relatively smooth to allow the cylinder 66 to be turned easily within the bore 56.

The top end of the cylinder 66 is in the form of an annular cap 84 and handle means 86. The annular cap 84 is integrally formed from the cylinder 66 and includes a flanged member 88 which rests on the top surface 58 of the port assembly 40. The flange 88 of the cap 84 is of a larger diameter than the bore 56 to prevent the cylinder 66 from sliding downwardly through the bore, thus maintaining the desired vertical alignment between the horizontal leg of the exhaust passage 60 and the valve opening 68 of the cylinder 66.

The handle means 86 is situated above and adjacent the cap 84 and comprises a horizontally disposed stem 90 inserted through and frictionally engaged to a horizontally disposed hole 92 extending through the cylinder 66.

As can be appreciated from FIG. 4, when the valve opening 68 is turned so that the valve opening 68 is generally at right angles to the passage leg portion 60, the passageway 52 is blocked to interrupt the flow of gas from the exhaust port passage 52 to the exhaust port outlet opening 50.

As can be appreciated from FIG. 6, manual rotation of the handle means 86 to a position where the exhaust port valve opening 68 is partially aligned with the exhaust port passage 52, (i.e., the valve is set to be partially open) enables a predetermined amount of gas to pass from the exhaust port passage 52 through the valve opening 68, and then out the exhaust port outlet opening 50.

Obviously, a maximum amount of gas passes through the exhaust port 28 when the valve opening 68 is rotated to be precisely, radially aligned with the horizontal portion 60 of the exhaust port passage.

Although omitted from the drawing (in the interest of drawing simplicity), the preferred embodiment of the invention uses a valve 64 which includes ratcheting means and indicator (indicia) means to enable one to rotate and hold the exhaust port valve in any number of various predetermined positions or settings, as desired.

Referring to FIGS. 3 and 7, the details of the couplings 25 and 27 can be seen. To that end, each comprises an essentially hollow tubular member including an externally threaded end 96, threadingly engaged in a respective opening in the port assembly block 41. In this regard, couplings 25 and 27 are mounted on sides 98 and 100, respectively, of the port assembly block 41. The coupling 27 also includes a pressure relief valve 99 which shall be discussed below.

The coupling 25 is threadingly engaged in an internally threaded opening on the side 98 of the port assembly block and in communication with the vertical passage 42. Similarly, the coupling 27 is threadingly engaged in an internally threaded opening on the side 100 of the port assembly block and in fluid communication with the vertical passage 45.

Although the hollow passageways in the respective couplings 25 and 27 are of a constant diameter, as shown in FIG. 3, each coupling has a thickened base portion 102 which tapers to a relatively narrow diameter intermediate section 104 and terminates in a slightly thickened end portion 106. In that regard, a hose or other gas transporting conduit is attached to either the coupling 25 or 27 by sliding the open end of the hose over the thickened end and onto the relatively thin intermediate section 104. The thickened end portion 106 of the coupling prevents its hose from readily pulling loose. Moreover, the increased thickness of the base portion 102 of the coupling ensures that there is a gas-tight seal between the hose and the coupling.

In order to preclude the possibility of accidentally overinflating the patient's lungs, the device 20 includes the heretofore mentioned pressure relief valve 99. That valve is a conventional pressure relief device and is connected on the coupling 27 in fluid communication with a relief valve opening (not shown), extending through the base portion 102 of the coupling 27. The valve is constructed so that whenever the gas pressure within the outlet port 26 exceeds a predetermined level, the valve pops open, thereby venting the outlet coupling 27 (and thus the patient's respiratory system as well), into the ambient atmosphere.

The amount of pressure necessary to cause the valve 99 to pop open is readily adjustable through calibration means 111, thus enabling the operator of the device to set or calibrate the pressure relief valve before connecting the respirator device 20 to the patient.

As shown in FIG. 2, the port assembly block 41 includes a flanged base 108 which attaches to the top surface 105 of the body 22 by means of two pins 109 and four hex nuts 110. Each pin 109 passes through a corresponding hole 111A in the metering plate 32 and then fits into a corresponding hole 111B in the top surface of the device's body 22. Similarly, each hex nut 110 is inserted through a corresponding hole 112 in the base portion 108 of the port assembly, passes through a corresponding hole 113A in the metering plate 32 and then is threaded into a corresponding internally threaded hole 113B on the top surface of the device's body 22 to secure the port assembly 40 in place.

The rotational means 34 includes a gear train 117 and a motor 132 which are attached to the motor-gear assembly 38. To that end, the motor-gear assembly 38 includes a hollow, generally elliptical chamber 114 in its front portion 116, and in which the gear train 117 is housed. The motor 132 is fixedly mounted on the rear portion 130 of the assembly 38.

Referring to FIG. 4, the gear train 117 comprises a plurality of interconnected gears 118, 119, 120, 121, 122, 123 and 124, respectively, and serves as a rotary speed reduction system for the device. The gear 118 is rotatably attached to the drive shaft 126 of the motor 132 and is connected to the gear 124, through the interconnecting reduction gears 119, 120, 121, 122 and 123, respectively, so that the speed of rotation of gear 124 is substantially less than that of the motor's shaft. The gear 124 is connected through a cylindrical drive shaft 128 to the cylinder 30. In that regard, the gear 124 is connected to a first end of the drive shaft 128. The second end of the drive shaft 128 extends through the rear surface 130 of the motor-gear assembly 38 (shown in FIG. 2) and into a cylinder bore 150 within the body 22 (when the front plate and the body are together).

As shown in FIGS. 2 and 5, the second end of the drive shaft 128 includes rotatable head 131 having a protruding slot 133. The protruding slot 133 of the rotatable head 131 mates with one end of the slotted valve cylinder 30 (in a manner to be described later) to cause the cylinder to rotate at the same rotational speed as shaft 28, and thus at some predetermined percentage of the rotational speed of the motor 132.

The motor 132 is a conventional 1.5 to 4.5 volt Direct Current electrical motor which, as mentioned above, is connected through the motor drive shaft 126 to the first gear 118 of the gear assembly. The barrel or casing 135 of the motor is fixedly attached to the rear surface 130 of the assembly 38 with the motor's drive shaft 126 extending through a hole in the rear surface 130 of the assembly and into gear chamber 114 for attachment to the first gear 118 of the gear train.

On the rear surface of the barrel 135 of the motor are two electrical contacts 134 (shown in FIG. 2) which are arranged to electrically engage corresponding electrical contacts (to be described later) situated within the body 22 of the device to supply the motor with electrical current.

A transparent plexiglass window 136 (shown in FIG. 1) is adhesively attached to the front surface 116 of the motor-gear assembly in order to cover and enclose the gear chamber 114. The window, thus protects the mechanical parts housed within the gear chamber, yet enables the operator of the device to view the operation of the gears 117, while the device is in operation.

A pair of screw holes 141 extend completely through the motor-gear assembly 38 (normal to its front and rear surfaces 116 and 130, respectively, with respective bolts 143 located therein to secure the assembly to the body 22 of the device by threadingly engaging corresponding internally threaded holes 145 in the body 22. The body 22 is mounted on a generally planar base 138.

Referring to FIG. 4, the base 138 comprises a top plate 140 and a bottom plate 142. The top plate 140 is constructed of a transparent plastic material, and is adhesively attached to the bottom plate 142, which is constructed of a resilient material, e.g., rubber. The rubber bottom plate 142 both insulates (electrically as well as thermally) the device 20 from the surface upon which the device is resting and operates as gripping means, preventing the device from accidentally sliding therealong. As shown in FIG. 2, the base 138 is sufficiently long to not only cover the entire bottom surface of the upper portion of the body 22 but to also extend beyond the front surface of the body to enable the motor gear assembly 38 to also rest thereupon when it is secured in an operational position to the body.

The body 22 includes a front surface 139 to which the motor-gear assembly 38 is secured and includes six cylindrical openings or chambers, namely, cylinder chamber 150 (as mentioned above), motor chamber 182, two heating element chambers 185 and two battery chambers 186.

The cylinder chamber 150 extends horizontally through the body 22 from the front surface 139 to the rear surface 152. The open end of the cylinder chamber 150 along the front surface 139 of the body is aligned with the head 131 of the drive shaft 128 when the motor-gear assembly 38 is attached to the body 22.

Moreover, when the port assembly is attached in place, the chamber 150 is situated directly below the inlet port, the outlet port and the exhaust port passage openings 43, 47 and 54, respectively. To that end, as shown in FIGS. 4 and 5, the inlet port passage opening 43, the outlet port passage opening 47 and the exhaust port passage opening 54 are in axial alignment with three openings in the top surface 105 of the body 22, namely, inlet port passage aperture 154, outlet port passage aperture 156 and exhaust port passage aperture 158, respectively.

Both the inlet port passage aperture 154 and the exhaust port passage aperture 158 are circularly shaped, with their diameter corresponding to the diameter of the respective passage openings 54 and 43, through the port assembly. The outlet port passage aperture 156 is generally rectangularly shaped, thus generally corresponding in size and shape to the outlet port passage opening 47 in the port assembly body 41. Each of these apertures 154, 156 and 158 is in fluid communication with respective portions of the cylinder chamber 150, thus providing a means of fluid communication between respective ports, via respective portions of the slotted cylinder 30 contained within the cylinder chamber 150, as will be described later.

The diameter of the slotted cylinder 30 is nearly equal but slightly less than the diameter of the chamber 150 (i.e., the cylinder 30 substantially fills the chamber's cross sectional area). However, there is a small amount of space between the periphery of the cylinder 30 and the cylinder chamber 150, thus enabling the cylinder to freely rotate within the chamber. Moreover, a small amount of gas is able to pass between the periphery of the cylinder 30 and the wall of the chamber 150.

As shown in FIG. 4, the front end of the cylinder chamber 150, is in the form of an annular lip 160 having a bore whose diameter is less than the diameter of the cylinder 30 to prevent the cylinder 30 from sliding out the front of the body.

The front portion of the cylinder 30 includes a slotted head 162 which is of a lesser diameter than the diameter of the remaining portion of the cylinder and extends through the bore of the annular lip 160 for receipt of the end 133 of the gear train shaft. Thus, rotation of the drive shaft 128 produces corresponding rotation of the slotted cylinder 30.

As shown in FIG. 5, a cylinder cap 164 seals the rear end of chamber 150. The cylinder cap 164 comprises an externally threaded bolt 165 having an enlarged knurled head 167 to serve as means to enable one to manually engage or disengage the cap 164 from the chamber.

Moreover, the free end of the bolt 165 acts as a stop against the adjacent end of the cylinder 30 to ensure that the cylinder is properly located with shaft end 133 located within its slot 162. As a result, the cylinder 30 is prevented from shifting longitudinally within the cylinder chamber and becoming disengaged from the rotatable drive shaft 128.

As shown in FIG. 5, the slotted cylinder 30 includes a pair of slots 170 and 172 which serve as the means for alternatively interconnecting the inlet port 24 with the outlet port 26 and the outlet port with the exhaust port 28. Each slot is an elongated recess extending longitudinally in the cylinder's peripheral surface 173. In particular, the inlet port slot 170 is situated at a generally opposite radial position along the periphery 173 of the cylinder from the exhaust port slot 172. In addition, the slot 170 and the slot 172 are each situated at different longitudinal positions along the length of the cylinder, as well. In particular, the slot 170 is longitudinally positioned along the cylinder's cylindrical surface 173 to enable it to bridge (be in simultaneous fluid communication with) both the outlet port aperture 156 and the inlet port aperture 154 during the inspiratory phase of the rotational cycle of the cylinder 30. As a result, the slot 170 connects the inlet port passage 42 with the outlet port passage 45 during this portion of the cycle.

Similarly, as shown in FIG. 4, the exhaust port slot 172 is longitudinally positioned along the cylindrical surface 173 of the cylinder 30 so that during an expiratory phase of the cylinder's rotational cycle, when the exhaust port slot 172 is adjacent the top surface of the body, the exhaust port slot 172 bridges both the exhaust port aperture 158 and the outlet port aperture 156. As a result, the slot 172 operates to connect the exhaust port passage 52 with the outlet port passage 45 during this portion of the cycle.

Referring to FIGS. 9 and 10, each slot 170 and 172, is a generally rectangularly shaped recess in the cylinder's peripheral surface 173. To that end, each slot comprises a pair of longitudinal side surfaces 174 cut radially through the cylinder's periphery 173 and a pair of lateral arcuate sides 176 interconnecting the two longitudinal surfaces 174 and an arcuate floor 178. Consequently, there is no direct fluid communication between the inlet port slot 170 on the one side of the cylinder and the exhaust port slot 172 on its opposite side, notwithstanding the slight amount of leakage which occurs between the periphery of the cylinder 30 and the bore 150, as will be described later.

It should be pointed out at this juncture that the exact size and shape of the slots 170 and 172, respectively, can be varied in order to change the flow characteristics of the gas passing therethrough (as shall be discussed later).

When the inlet port slot 170 is bridging the inlet port aperture 154 and the outlet port aperture 156 (as shown in FIG. 5), gas is enabled to flow from the inlet port passage 42, through the slot 170, to the outlet port passage 45. Likewise, when the exhaust port slot 172 bridges the exhaust port aperture 158 and the outlet port aperture 156, gas is permitted to flow from the outlet port passage 45, through the slot 172, to the exhaust port passage 52.

As mentioned above, a slight amount of gas leakage occurs through the interface between the periphery of the cylinder 30 and the cylinder chamber 150. This feature is of importance to ensure that there is maintained a minimum threshold pressure, commonly referred to as positive end pressure, regardless of the rotational position to prevent the patient's lungs from collapsing due to excessive exhalation, in the event that the exhaust port valve is improperly set.

As mentioned above, the body 22 includes a chamber 182 for receiving the projecting portion of the motor 132 when the motor-gear assembly 38 is secured to the body 22. When so connected, the bulk of the motor rests within the chamber 182 such that the electrical contacts 134 on the rear surface of the motor electrically contact a second pair of electrical contacts 183 located at the base 184 of the motor chamber. Thus, the motor is automatically disconnected from the source of electricity when the motor-gear assembly 38 is removed from the body 22, and is automatically re-connected to that source when that assembly is re-attached.

As mentioned above, the body 22 also includes two battery chambers 186, each of which is configured to receive a conventional size AA storage battery 187. It should be pointed out that the device 20 may readily be adapted to use any type of battery, if portability is desired or can be adapted to be powered from AC lines, via the use of appropriate circuitry, if desired.

A pair of electrical contacting caps 188 holds the batteries 187 in place within their respective chambers 186 and also function as the means for electrically connecting the battery terminals to the control means 33, (which shall be discussed below). The two electrical caps 188 electrically contact the positive pole of one battery and the negative pole of the other battery, respectively. In that regard, the opposite pole of each of the respective batteries are interconnected within the housing by means of a conventional electrical conductor 191. Other electrical conductors (not shown) connect each cap 188 to an associated terminal of the control means 33 to complete the electrical circuit.

In one embodiment of the invention, the control means 33 comprises a potentiometer (not shown) which is electrically connected in series between the motor 132 and the pair of batteries 187. As can be seen, the potentiometer includes an adjustment knob 189 which is situated on one side of the body 22. In that regard, the knob is connected to the slider of the potentiometer so that when the knob is rotated, the electrical resistance of the circuit connecting the motor 132 to the electrical source 187 is increased or decreased (depending upon the direction of rotation of the knob), thus varying the amount of current being supplied to the motor. Obviously, the greater the amount of current being supplied to the motor, the greater is the rotational speed of both the motor and the slotted cylinder 30.

An alternative and preferred embodiment of the invention utilizes control means 33 comprising a microprocessor unit (not shown) housed within the device 20 and which is programmed to enable the operator of the respirator device 20 to instantly select any predetermined rotational speed desired for the cylinder by adjustment of the knob 189 or other suitable selector means. Furthermore, the microprocessor is also programmed to provide intermittent (i.e., stop and go) rotational movement of the cylinder, as desired.

The metering means 32 is a member arranged to be mounted between the bottom surface 62 of the port assembly and the top surface 105 of the body to establish the maximum size and shape of the opening between apertures 154, 156 and 158 in the body 22 and passageway openings 54, 47 and 43, respectively, in the port assembly 40. This feature enables one to establish the flow characteristics of the device by appropriate selection of the metering means. In the embodiment shown, the metering means comprises a generally planar plate having an inlet aperture 194, an outlet aperture 196 and an exhaust aperture 198, as well as a plurality of mounting holes 111A and 113A.

The inlet aperture 194 of the plate 32 is aligned with the inlet passage aperture 154 in the body 22, the outlet aperture 196 is aligned with the outlet passage aperture 156 and the exhaust port aperture 198 is aligned with the exhaust port aperture 158.

The metering plate 32 enables the operator of the respirator device 20 to readily change the effective size and shape of the aperture openings between the cylinder chamber 150 and the port assembly 40 by merely substituting one interchangable metering plate for another, with each of said plates having one or more different size or shape apertures.

Although the metering plate 32 (shown in FIG. 2), comprises three apertures 194, 196 and 198 which correspond in both size and shape to the three apertures 154, 156 and 158, respectively, through the body, such a construction is only one of various arrangements possible within the scope of this invention.

As mentioned above, the volume and flow characteristics of gas passing through the respirator device can be readily changed by changing either or both the slotted cylinder 30 and the metering plate 32 being used.

To that end, by removing the cylinder cap 164 from the body 22, the cylinder 30 can readily be removed for purposes of substitution, servicing or cleaning as desired. Similarly, by removing the hex nuts 110, the port assembly 40 is readily removed in order that the metering plate 32 may also be removed or replaced as desired.

With regard to changing the cylinder, the flow characteristics produced by a particular cylinder is readily changed by changing the size, shape or number of slots it contains, by using differently constructed (e.g., ribbed) slots or by changing the slots' radial position along the cylinder.

An example of an alternatively constructed valve cylinder 30B is shown in FIG. 11. This cylinder is used to produce a pulsating gas flow when it is used in combination with a metering plate 32B which has a single narrow inlet port aperture slit 194B. Cylinder 30B comprises a plurality of parallel, evenly spaced ribs 200 running longitudinally along a portion (approximately one-half the length) of the inlet port slot 170B. Formed between the respective ribs are corresponding parallel slits 202 which receive and then channel gas therealong. The ribs 200 and slits 202 are situated within the slot 170B adjacent the aperture 194B of the metering plate 32B during the inspiratory portion of the cylinder's rotational cycle.

Operation of this embodiment can best be appreciated by reference to FIGS. 11 and 12. To that end, a single pulse of air enters the slot 170B as each respective slit 202 successively rotates into fluid communication with the aperture slit 194B. Thus, successive resulting pulses of gas are produced and flow toward the aperture 196B of the metering plate, through the passage aperture 156 and finally toward the outlet port 26, as each successive slit 202 rotates into fluid communication with the metering plate aperture slit 194B.

It should further be appreciated that when the metering plate 32B and cylinder 30B are used in combination with each other, as described above, only the inspiratory portion of the respiratory cycle is affected. However, if deemed medically desirable, the exhalation portion of the cycle could also be modified, as desired.

Another example of how the flow characteristics of the gas passing from the inport 24 to the outport 26 of the device 20 is modified (in this case without substituting cylinders 30), by using still another interchangable metering plate 30C, is shown in FIG. 13. The metering plate 30C comprises an inlet aperture 194C which increases from a narrow opening to a large opening going from right to left, transverse to the longitudinal direction of the plate. Thus, it should readily be appreciated, that as the slot 170 of the cylinder rotates (in a counter clockwise direction) into fluid communication with the opening 194C, the slot 170 initially communicates with the passage 42 through only a very narrow opening. As the cylinder continues to rotate, said opening gradually enlarges, thus placing slot 170 in communication with an increasingly larger portion of the aperture 194C as well as a correspondingly larger portion of the passage opening 43. As a result of the foregoing, a graduated flow of gas, from a small volume to a large one, is produced during each rotational cycle. Accordingly, the volume of gas flowing from the inlet port passage 42 to the outlet port 26 of the device 20 increases during the inspiration phase.

It should be pointed out that the volume of gas passing from the inlet port 24 to the outlet port 26 may also readily be changed by changing only the size of the respective apertures, thus keeping their shape unchanged.

One type of medical treatment for which the respirator device 20 is ideally adapted is known as high frequency ventilation. High frequency ventilation entails providing a patient with short bursts or pulses of air at regular, high frequency intervals (e.g., one thousand pulses per minute). In that regard, the cylinder 30B and the metering plate 32B, (both shown in FIG. 12) are well adapted for use in a high frequency ventilation application since a plurality of pulses of gas are produced during each rotational cycle of the cylinder (with the number of pulses corresponding to the number of slits 202 formed within the slot 170B). Moreover, the frequency of ventilation can be increased by either increasing the rotational speed of the cylinder or by increasing the number of ribs comprising the inlet slot(s).

As will be appreciated by those skilled in the art, the flow characteristics produced by the various different metering means and the slotted cylinders described herein are merely exemplary. Thus, other metering means and cylinders can be used to produce any desired flow characteristic. For this reason, the device 20 is ideally suited for veterinary use since the flow characteristics produceable by the device can be tailored to meet the respiratory needs of a wide variety of different species of animal.

Referring to FIG. 2, contained within the two heating element chambers 185 (which are adjacent and parallel to the cylinder chamber 150) are a pair of electrical heating elements 35. Each heating element 35 is a conventional device and comprises an elongated electrical heating unit (e.g., a nichrom or ceramic heater) which is connected through an electrical conductor to the batteries 187. The heating elements 35 operate to heat the body 22, the cylinder 30, the metering means 32 and the port asbly 40 of the device 20 in order to prevent condensation of the gas from occurring as it passes through the device.

The device 20 further comprises first indicator means 204, e.g., a light emitting diode, arranged to indicate battery failure and second indicator means, e.g., a light emitting diode, 206 arranged to signal a malfunction in the operation of the motor and gear assembly 34. The indicator means 204 and 206, may also include conventional annuciator means to provide an audible warning signal, as well as the visual warning signal.

In accordance with the preferred embodiment of the invention, the body 22 (except for its base 138), the front plate 38, the port assembly 40 and the metering plate 32 are generally constructed of a strong, durable plastic such as acrylonitrile-butadiene-styrene (ABS), the gears 117 are constructed of nylon and the rotatable cylinder 30 is constructed of an extrudable, molded flourocarbon plastic such as Teflon (sold by E. I. Dupont de Nemours of Wilmington, Del.). However, the device 20 may be alternatively constructed of a wide variety of different plastics, metals or other materials.

Although the metering means 32 of the preferred embodiment of the invention comprises a replaceable metering plate 32, alternative embodiments of the invention (not shown) include other means which do not include replaceable plates, for adjusting the flow characteristics of the gas passing through the device 20, e.g., metering means having a sliding aperture.

As can readily be appreciated from the foregoing discussion, the device 20 is extremely compact and thus, is well adapted for portable use. Moreover, its modular construction enables the various components of the device 20 to be quickly and easily removed in order that they may be repaired, replaced or cleaned, as desired. In that regard in order to quickly recognize and remedy a malfunction should one occur, the device includes a transparent window 136 which enables the operator of the device to readily observe various moveable components of the device 20 while they are in operation.

Without further elaboration the foregoing will so fully illustrate my invention that others may, by applying current or future knowledge, readily adapt the same for use under various conditions of service.

I claim:

1. A valve respirator device comprising a housing having a bore extending therein, said housing also having first, second and third passage means each having one portion communicating with said bore and a second portion communicating with a first, a second and a third port, respectively, wherein said first port is adapted to be in fluid communication with a source of gas, said second port is open to the ambient atmosphere and said third port is adapted to be in fluid communication with a patient's respiratory system, movable means in the form of a readily replacable rotatable cylinder mounted in said bore having a first recess in alignment with said first and third passage means; and a second recess in alignment with said second and third passage means, both recesses being located in the cylinder's periphery and isolated from each other, for alternately establishing fluid communication, first between said first port and said third port during a portion of a rotational cycle of said cylinder when said first recess is in fluid communication with both said first passage means and said third passage means and then between said second port and said third port during a second portion of said rotational cycle during which time said second recess is in fluid communication with both said second passage means and said third passage means, such that when said first port is in fluid communication with said third port, said patient inhales the gas passing through said first port and when said second port is in fluid communication with said third port, said patient is able to exhale gas therethrough to the atmosphere, means for controlling the amount of gas passing through each of said ports, with said means for controlling the passage of gas through said second port comprising adjustable valve means, capable of being adjusted while the device is in operation to control the patient's rate of exhalation and means for regulating the rotation of said cylinder and thereby the time intervals during which said first port and said second port, respectively, are in fluid communication with said third port.

2. The device of claim 1, wherein said recesses are located at different radial positions on said cylinder.

3. The device of claim 2, wherein said recesses are longitudinally spaced from each other.

4. The device of claim 1, wherein said means for controlling the amount of gas passing through each of said ports comprises an apertured metering plate mounted to said housing so as to intersect the path of fluid communication between at least one of said ports and said movable means, such that gas passing from that port to another of said ports passes through a particular aperture in said plate, with the flow characteristics of said gas passing therethrough being dependent upon the size and shape of said aperture.

5. The device of claim 4, wherein said plate is releasably secured to said device and constructed to be readily interchangeable with other releasably securable apertured metering plates in order to vary the flow characteristics of said gas passing through the plate secured to said device.

6. The device of claim 5, further comprising valve means for regulating the flow of gas through said second port, thus regulating the patient's exhalation rate.

7. The device of claim 5, further comprising a pressure relief valve which prevents excessive pressure from passing through said third port to said patient's respiratory system.

8. The device of claim 1, wherein said moveable means further comprises a motor which is coupled to said cylinder.

9. The device of claim 8, further comprising gear means connected between said motor means and said cylinder.

10. The device of claim 9, wherein said gear means comprises an assembly releasably secured to said motor means and said cylinder.

11. The device of claim 8, wherein, said gas is thermally isolated from said motor means as it passes through said device.

12. The device of claim 1, which is compact in size and portable in construction.

13. The device of claim 12, wherein said device is constructed from a plurality of modular assemblies capable of readily being assembled or disassembled to provide ready access to the various component parts of said device.

14. The device of claim 13, wherein said ports are located in a modular port assembly and said moveable means is located in a modular valve assembly.

15. The device of claim 14, additionally comprising a modular gear assembly.

16. The device of claim 15, wherein said gear assembly includes means for enabling the viewing of the operation of said gear assembly.

17. The device of claim 16, further comprising heating means for preventing the condensation of said gas from occurring as it flows through said device.

18. The device of claim 1, further comprising heating means for preventing condensation of said gas from occurring as it flows through said device.

19. The device of claim 1, further comprising indicator means for producing a warning signal to indicate a change in the rotational speed of said cylinder.

20. A valve respirator device comprising a housing having a passageway extending therein, said housing also having first, second and third passage means each one portion communicating with said passageway and a second portion communicating with a first, a second and a third port, respectively, wherein said first port is adapted to be in fluid communication with a source of gas, said second port is open to the ambient atmosphere and said third port is adapted to be in fluid communication with a patient's respiratory system, moveable means which includes a member mounted with respect to said passageway and having a recess in its periphery positioned to be aligned with either said first and third or said second and third passage means for alternately establishing fluid communication, first between said first port and said third port and then between said second port and said third port such that when said first port is in fluid communication with said third port, said patient inhales the gas passing through said first port and when said second port is in fluid communication with said third port, said patient is able to exhale gas therethrough to the atmosphere, means for controlling the amount of gas passing through each of said ports, said means for controlling the awmount of gas passing through each of said ports including an apertured metering plate connected to said housing so as to be positioned to intersect the path of fluid communication between at least one of said ports and said moveable means, such that gas passing from that port to another of said ports passes through an aperture in said plate with the flow characteristics of said gas passing therethrough being dependent upon the size and shape of said aperture and means for regulating the movement of said member and thereby time intervals during which said first port and said second port, respectively, are in fluid communication with said third port.

21. The device of claim 20, wherein said plate is releasably secured to said device and constructed to be readily interchangeable with other releasably securable apertured metering plates, in order to vary the flow characteristics of said gas passing through the plate secured to said device.

22. The device of claim 21, further comprising valve means for controlling the flow of gas through said second port, thus regulating the patient's exhalation rate.

23. The device of claim 21, further comprising a pressure relief valve which prevents excessive pressure from passing through said third port to said patient's respiratory system.

24. A valve respirator device comprising a housing having a bore extending therein, said housing also having first, second and third passage means each having one portion communicating with said bore and a second portion communicating with a first, a second and a third port, respectively, wherein said first port is adapted to be in fluid communication with a source of gas, said second port is open to the ambient atmosphere and said third port is adapted to be in fluid communication with a patient's respiratory system, moveable means in the form of a rotatable cylinder mounted in said bore of generally constant diameter having a first recess in alignment with said first and third passage means and a second recess in alignment with said second and third passage means, both recesses being located in the cylinder's periphery and isolated from each other, for alternatively establishing fluid communication, first between said first port and said third port during a first portion a rotational cycle of said cylinder when said first recess is in fluid communication with both said first port and said third port and then between said second port and said third port during a second portion of said rotational cycle during which time said second recesses is in fluid communication with both said second port and said third port, such that when said first port is in fluid communication with said third port, said patient inhales the gas passing through said first port and when said second port is in fluid communication with said third port, said patient is able to exhale gas therethrough to the atmosphere, means for controlling the amount of gas passing through each of said ports and means for regulating the rotation of said cylinder and thereby the time intervals during which said first port and said second port, respectively, are in fluid communication with said third port.

* * * * *